(12) United States Patent
Liu et al.

(10) Patent No.: US 12,023,053 B2
(45) Date of Patent: Jul. 2, 2024

(54) SYNDESMOSIS FIXATION AND RECONSTRUCTION SYSTEM AND METHOD OF USING THE SAME

(71) Applicant: The University of Toledo, Toledo, OH (US)

(72) Inventors: Jiayong Liu, Toledo, OH (US); David Dick, Toledo, OH (US); Vijay K. Goel, Toledo, OH (US); Nabil A. Ebraheim, Toledo, OH (US)

(73) Assignee: The University of Toledo, Toledo, OH (US)

(*) Notice: Subject to any disclaimer, the term of this patent is extended or adjusted under 35 U.S.C. 154(b) by 120 days.

(21) Appl. No.: 16/975,828

(22) PCT Filed: Feb. 26, 2019

(86) PCT No.: PCT/US2019/019519
§ 371 (c)(1),
(2) Date: Aug. 26, 2020

(87) PCT Pub. No.: WO2019/168817
PCT Pub. Date: Sep. 6, 2019

(65) Prior Publication Data
US 2020/0405329 A1    Dec. 31, 2020

Related U.S. Application Data

(60) Provisional application No. 62/635,682, filed on Feb. 27, 2018.

(51) Int. Cl.
*A61B 17/17* (2006.01)
*A61B 17/72* (2006.01)
(Continued)

(52) U.S. Cl.
CPC ...... *A61B 17/1775* (2016.11); *A61B 17/1725* (2013.01); *A61B 17/1796* (2013.01); *A61B 17/7241* (2013.01); *A61B 17/8635* (2013.01); *A61B 17/8645* (2013.01); *A61B 17/8869* (2013.01); *A61B 17/8886* (2013.01); *A61B 2017/681* (2013.01); *A61B 17/90* (2021.08)

(58) Field of Classification Search
CPC ............ A61B 17/1796; A61B 17/1725; A61B 17/1775; A61B 17/1764; A61B 17/1782; A61B 17/1739; A61B 17/1717; A61B 17/1714; A61B 17/7241
See application file for complete search history.

(56) References Cited

U.S. PATENT DOCUMENTS

| 5,334,205 A | * | 8/1994 | Cain | .................. A61B 17/1742 606/86 R |
| 5,766,174 A | * | 6/1998 | Perry | ................. A61B 17/1725 606/62 |

(Continued)

*Primary Examiner* — Amy R Sipp
(74) *Attorney, Agent, or Firm* — MacMillan, Sobanski & Todd, LLC

(57) ABSTRACT

A fixation/reconstruction system for treating syndesmotic ankle fractures includes a screw guide assembly configured to align the cannulated screw for insertion into, and securing within, the patients bone; and, a tension band alignment assembly configured to insert at least one tension band through a transverse opening in the patient s leg, and to secure the tension band.

17 Claims, 7 Drawing Sheets

(51) Int. Cl.
    *A61B 17/86*     (2006.01)
    *A61B 17/88*     (2006.01)
    A61B 17/68     (2006.01)
    A61B 17/90     (2006.01)

(56) References Cited

U.S. PATENT DOCUMENTS

| | | | | |
|---|---|---|---|---|
| 6,254,605 | B1 * | 7/2001 | Howell | A61B 17/1764 606/86 R |
| 2005/0107791 | A1 * | 5/2005 | Manderson | A61B 17/68 606/62 |
| 2010/0010490 | A1 * | 1/2010 | Brigido | A61B 17/1775 606/62 |
| 2014/0025121 | A1 * | 1/2014 | Foley | A61B 17/3421 606/279 |
| 2016/0089189 | A1 * | 3/2016 | Buscaglia | A61B 17/1725 606/64 |
| 2017/0112552 | A1 * | 4/2017 | Sinnott | A61B 17/863 |
| 2019/0000509 | A1 * | 1/2019 | Cowens | A61B 17/68 |
| 2021/0128203 | A1 * | 5/2021 | Vordemvenne | A61B 17/8685 |

* cited by examiner

SYNDESMOSIS FIXATION AND RECONSTRUCTION SYSTEM AND METHOD OF USING THE SAME

CROSS-REFERENCE TO RELATED APPLICATIONS

This application is a national stage application filed under 35 U.S.C. § 371 of international application PCT/US19/019,519, filed under the authority of the Patent Cooperation Treaty on Feb. 26, 2019, which claims the benefit of U.S. Provisional Application Ser. No. 62/635,682 filed Feb. 27, 2018, the entire disclosure of which is expressly incorporated herein by reference.

STATEMENT REGARDING FEDERALLY SPONSORED RESEARCH

The invention was not made with any U.S. Government support, and the United States Government has no rights in the invention.

BACKGROUND OF THE INVENTION

Syndesmotic ankle fractures are very common, with trans-syndesmotic fractures accounted for about two-thirds of all ankle fractures.

Currently used devices to treat such fractures include syndesmosis screws, Tightrope® and FiberWire® fixation devices by Arthex, Inc., intramedullary screws; intramedullary fibular nails, and cannulated screws. However, each of these devices has major drawbacks.

For example, a syndesmosis screw (static fixation system) must be combined with a fibular plate, which is relatively invasive, with increasing risk of complications such as infection, delayed union, nonunion, etc. especially for patients with significant soft tissue damage and comorbidities. This static fixation procedure requires 6-8 weeks of immobilization and non-weight-bearing following the procedure, which in turn causes delayed functional recovery. A second operation is required to remove the screw before weight-bearing. Otherwise, the screws may cause pain or limit mobility and could be broken when weight-bearing starts. Another complication is the possible reoccurrence of diastasis (separation) after screw removal.

Use of a Tightrope® fixation device (dynamic reconstruction system) alone results in no distal fibula fracture fixation function. Rather, this type of fixation device also requires fibula plate fixation, which is highly invasive as well. This device/procedure also has potential risk of complications, such as infection, delayed union, and the like.

Use of existing intramedullary screws also provide challenges. The syndesmosis screw is difficult to correctly position because the intramedullary screw is in the way, and a second operation is required to remove the syndesmosis screw before weight-bearing can occur.

Use of an intramedullary fibular nail also provides challenges. The intramedullary fibular nail requires a relatively invasive procedure in order to ream the nail canal. Also, a second operation is required to remove the syndesmosis screw before weight-bearing can occur. This device/procedure also has the potential risk of reoccurrence of diastasis (separation) after syndesmosis screw removal.

Use of a cannulated screw also provides challenges as the syndesmosis screw is difficult to correctly position due to the cannulated screw placement being in the way.

SUMMARY OF THE INVENTION

Described herein is a fixation/reconstruction system for treating syndesmotic ankle fractures that includes a screw guide assembly configured to align a cannulated screw for insertion into a patient's bone; and, a tension band alignment assembly configured to insert at least one tension band through a transverse opening in the patient's leg, and to secure the tension band.

In a first aspect, there is provided a fixation/reconstruction system for repairing syndesmotic ankle fractures that includes at least one cannulated screw having at least one transverse opening; at least one tension band; and, at least one or more fasteners for the tension band.

In certain embodiments, the cannulated screw, the tension band, and the fasteners are packaged as a sterilized kit.

In certain embodiments, the fixation/reconstruction system can further include one or more of: a screw-guide wire; a drill guide wire; and/or a screw driver.

In another aspect, there is provided herein a drill guide assembly for assisting in the insertion of at least one screw within a patient's fibula, and the insertion of at least one tension band through a transverse opening in the patient's leg.

In certain embodiments, the drill guide assembly has a channel for removably receiving a screw driver and a tightening mechanism to secure the screw driver.

In certain embodiments, the drill assembly includes a drill guide bushing assembly and a cannulated drill bit guide.

In another aspect, there are provided herein different types of screws useful with the fixation/reconstruction system, and also useful in other surgical procedures.

In another aspect, there is provided herein a method for treating syndesmotic ankle fractures, comprising:
  inserting a cannulated screw into the intramedullary space of the distal fibula;
  guiding a first end of the tension band through a passage in fibula, an opening in the cannulated screw, a passage in the tibia, and retrieving the tension band on the medial side of the tibia;
  placing a first fastener along a central portion the tension band;
  guiding the first end of the tension band back through the tibia, the opening in the cannulated screw, and the fibula;
  placing a second fastener on the first and second ends of the tension band; and,
  securing the first and second ends of the tension band, thereby allowing tightening and treatment of the syndesmosis.

Other systems, methods, features, and advantages of the present invention will be or will become apparent to one with skill in the art upon examination of the following drawings and detailed description. It is intended that all such additional systems, methods, features, and advantages be included within this description, be within the scope of the present invention, and be protected by the accompanying claims.

DETAILED DESCRIPTION

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

Described herein is an improvement in the field of orthopedics in the treatment of syndesmotic ankle fractures without the need for very invasive procedures, generally referred to herein as Syndesmotic Ankle Fracture Fixation and Reconstruction (SAFFR) fixation/reconstruction system.

The SAFFR fixation/reconstruction system 10 is useful to achieve reduction and fixation of distal fibular fractures, and reconstruction of disrupted syndesmotic ligaments simultaneously. Further, the SAFFR fixation/reconstruction system 10 does not require an additional surgery for removal of the device.

Use of the SAFFR fixation/reconstruction system 10 allows for earlier physiologic motion of the ankle and syndesmosis following fixation and reconstruction. Also, use of the SAFFR fixation/reconstruction system 10 supports early weight-bearing and accelerated rehabilitation and recovery.

The SAFFR fixation/reconstruction system 10 allows percutaneous insertion, and may be safely used in high-risk patients, such as patients with significant comorbidities and soft tissue damage.

Implementation of the SAFFR fixation/reconstruction system 10 can achieve faster fracture healing and decrease chances of complications such as infection and delayed union or non-union, due to its minimally invasive approach and reliable fixation and reconstruction features.

The SAFFR fixation/reconstruction system can save up to two third or three fourth of current costs per patient, not counting the savings from the cost of complications.

The SAFFR fixation/reconstruction system is also used transversely/obliquely insert one or more tension bands through the patient, as further explained herein. The tension band can be made of a flexible wire, cable, woven or nonwoven, metallic or synthetic material. The tension band serves as syndesmosis ligaments function to maintain the normal distal tibiofibular articulation and ankle joint.

The tension band protects the torn syndesmosis joint by preventing distraction of the fibula from the tibia while allowing normal articulation of the joint. The tension band also provides appropriate healing circumstance for the distal fibular fracture and disrupted syndesmotic ligaments.

Figure 1A:
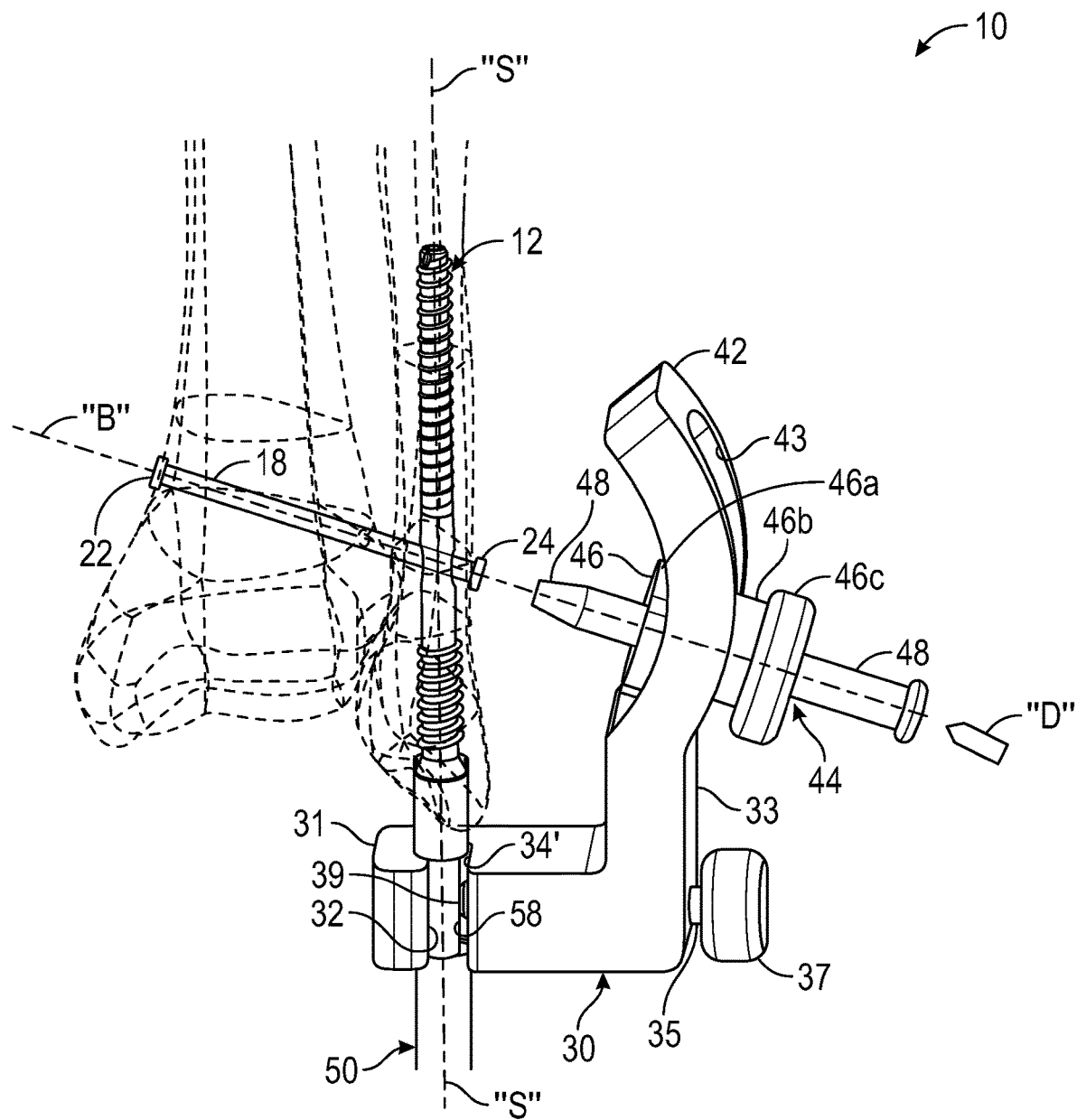
FIG. 1A. Schematic perspective view (with bones in phantom) of a fixation/reconstruction device with a cannulated screw, showing a driver, drill guide assembly, and guide wires trajectories.

Referring first to FIG. 1, a composite schematic illustration of the SAFFR reduction/fixation device is shown with all elements/steps shown in a single illustration. It is to be understood, however that the various elements of the SAFFR device/system and the various steps would be used/performed in a particular order, not as illustrated in FIG. 1A.

The fixation/reconstruction SAFFR system 10 is useful both to insert a cannulated screw 12 into a patient's bone, and to insert a tension band 18 through the patient's leg.

The cannulated screw 12 is inserted into the distal end of the fibula, and is passed up the intramedullary canal. The cannulated screw 12 has a slot 13 on a first end 12a, at least one transverse opening 14, and an axial opening 15 extending from the first end 12a to a second end 12b of the screw 12.

In order to secure the tension band 18, a first end of the tension band 18 passes through the fibula and the transverse opening 14 in the screw 12, through the tibia, and through the skin on the medial side of the ankle. A second end of the tension band 18 remains outside of the patient. It is to be understood that, in certain end use applications (depending on the fixation needed), one or more tension bands 18 can be used, as further explained herein.

Figure 1B:
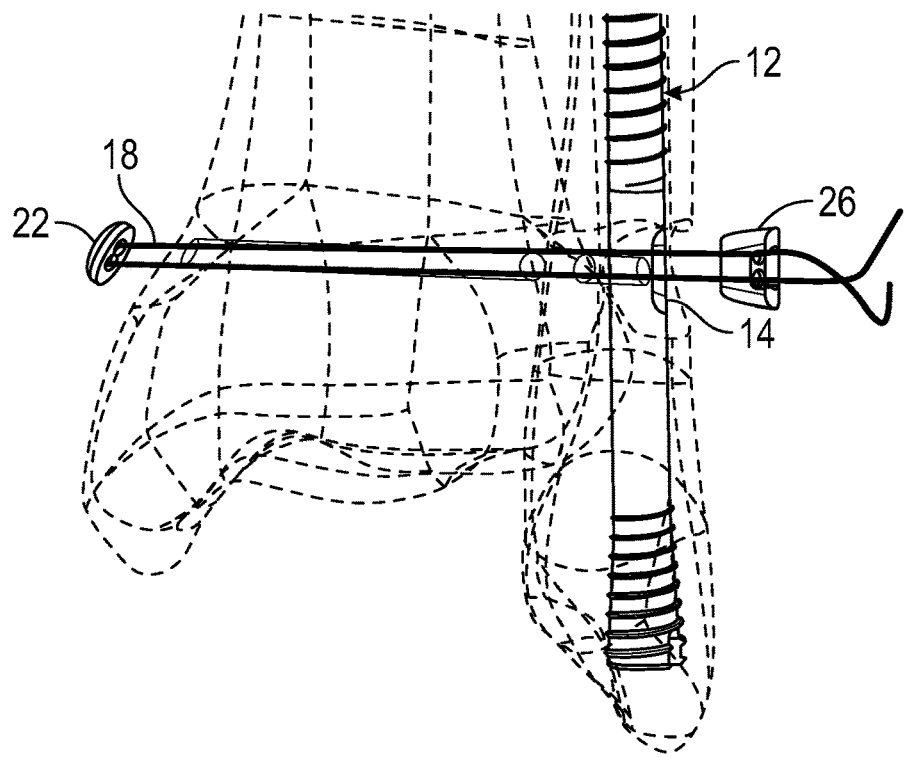
FIG. 1B. Schematic exploded perspective view (with bones in phantom) showing a cannulated screw, a tension band and fasteners at a point during a surgical procedure.
Figure 1C:
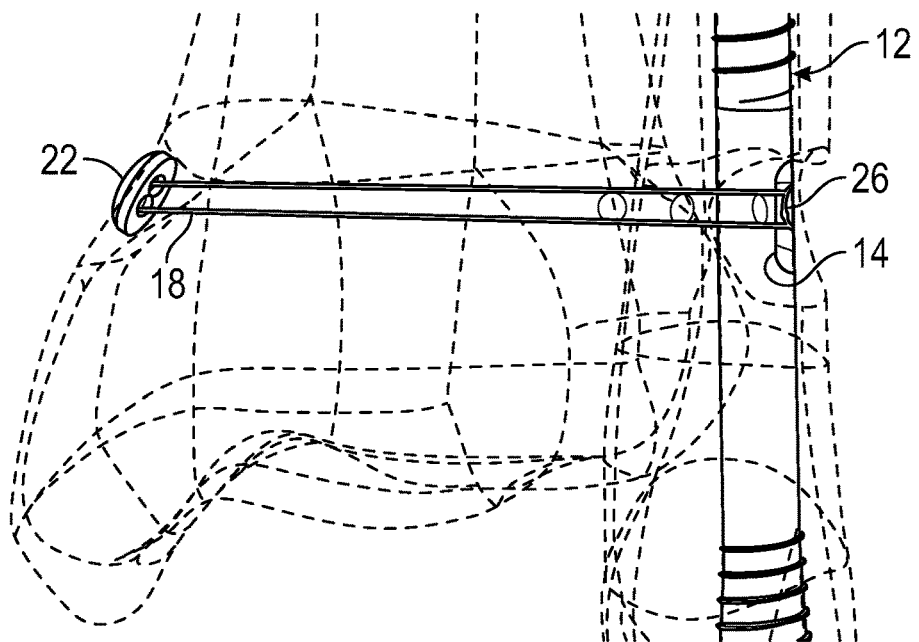
FIG. 1C. Schematic exploded perspective view (with bones in phantom) showing a cannulated screw, a tension band and fasteners after completion of a surgical procedure.

As shown in FIGS. 1B-1C, a middle portion of the tension band 18 is secured to the medial aspect of the tibia with a first fastener 22 such as a button. While the fastener 22 in the embodiment shown is a button, it is within the contemplated scope of the present invention, that in other embodiments, other types of suitable fasteners can be used to secure the tension band, as further explained herein. This first fastener 22 may be provided with holes or other means to attach the tension band 18, and allows the tension band 18 to later be tensioned. This first fastener 22 can be introduced with the tension band 18 and be deployed with a toggling action, or, if the medial skin is breached, introduced from the medial side of the tibia. Once this first fastener 22 is in place, a first end of the tension band 18 passed back through the tibia, screw, fibula and out of the patient's leg.

The physician pulls the first end of the tension band tension 18, pulling the tibia and fibula together into the correct position. Then, second fastener 24 is introduced to the lateral side of the fibula and secured to the second end of the tension band 18, maintaining the required tension. If damage to the fibula in this area prevents securing the second fastener 24 to the bone, the second fastener 24 could also be secured directly to the screw 12.

Figure 2A:
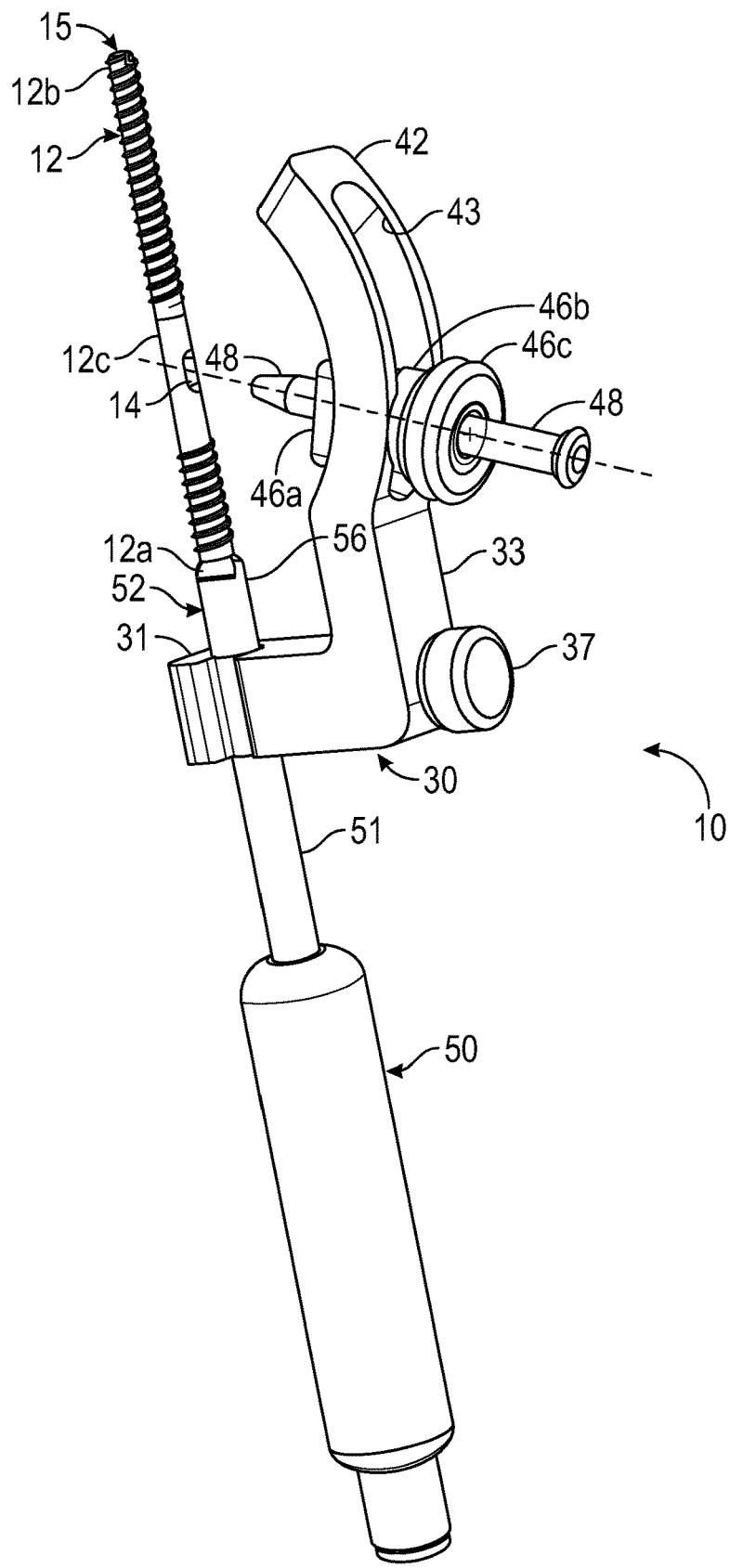
FIG. 2A. Schematic perspective view of a fixation/reconstruction device with a cannulated screw, showing a driver, drill guide assembly, and drill trajectory.
Figure 2B:
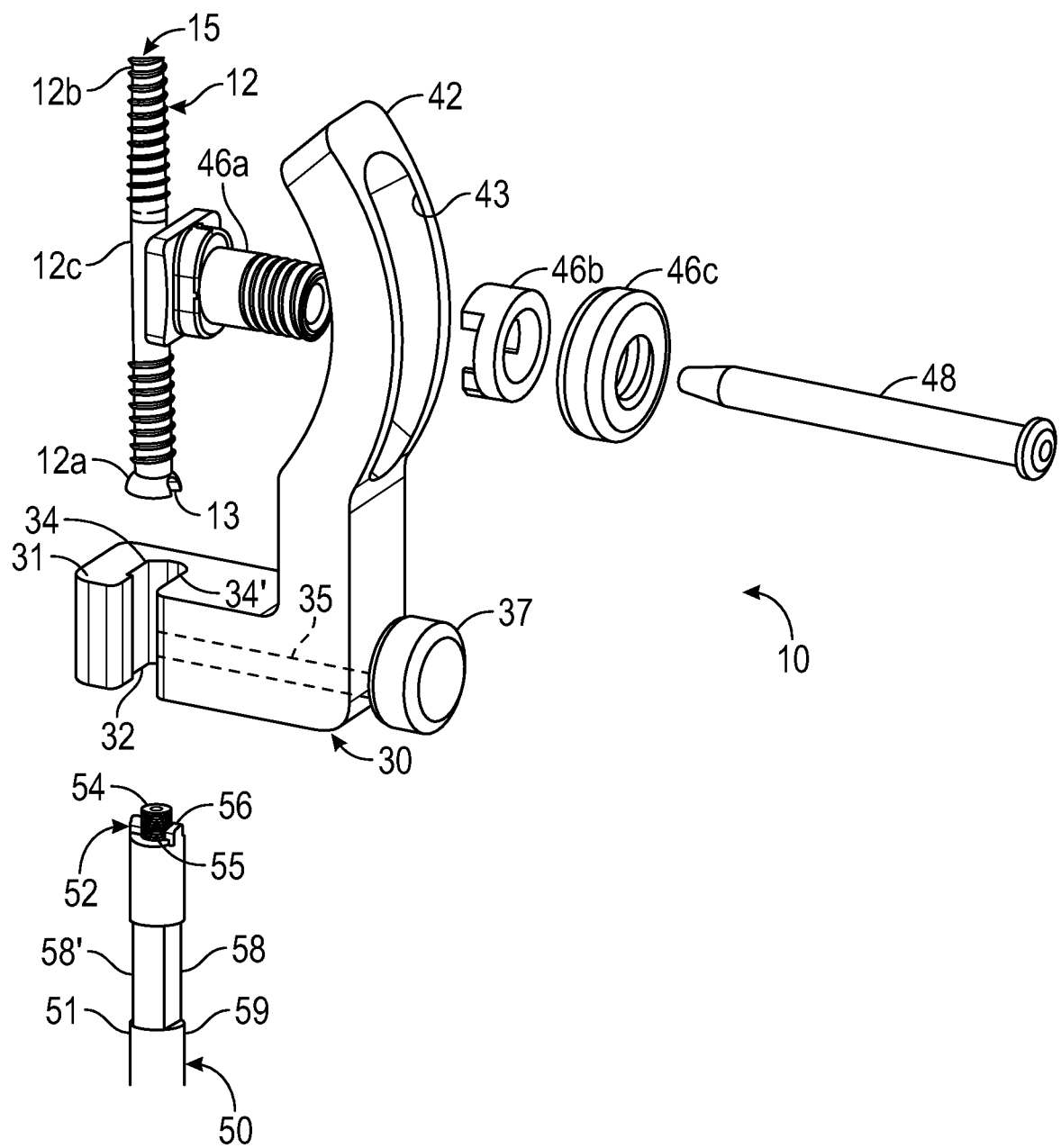
FIG. 2B. Schematic perspective exploded view, partially broken away, of a fixation/reconstruction device with a cannulated screw, showing a driver, drill guide assembly.

Referring now to FIGS. 2A-2B, one embodiment of the SAFFR fixation/reconstruction system 10 showing an intermedulary screw 12, a screw driver 50, and a drill guide assembly 30.

In use, the drill guide assembly 30 is used to make on opening to allow the insertion of the tension band 18 through a transverse opening in the patient's leg, and to secure (and tighten) the tension band 18.

In order to most easily describe the SAFFR fixation/reconstruction system 10, reference is made to FIGS. 2A-2B in combination with FIG. 1, and with the following general description of how the surgeon will achieve the fixation/reconstruction procedure.

After the fracture has been externally reduced as far as possible by the physician, a screw-guide wire "S" is used to penetrate the distal end of the fibula, and is passed up the intramedullary canal. A screw driver 50 having a shaft 51 and a tip 52 is used to insert a screw 12 (having an axially extending opening 15 extending therethrough, as best seen in FIGS. 3-6) into the patient. The screw 12 is removably secured to the tip 52 of the screw driver 50, then slipped over the exposed end of the screw-guide wire "S" extending from the patient. The exposed end of the screw-guide wire "S" is thus axially positioned within the axially extending opening 15 in the screw 12.

The screw 12 is turned using the driver 50, following the screw-guide wire "S", and is stopped when the desired depth is achieved.

The screw 12 is removably held to the tip 52 of the driver 50 by an axially extending threaded tightening mechanism 54. Opposing ears 56 on the driver tip 52 engage the slot 13 on the screw head 12a, providing a means to transmit torque to drive the screw 12 and to align the screw 12 to the screw guide assembly 30. The tip 52 can have opposing flat surfaces 55 that can be secured against a conforming flat surface in of the head 12a of the screw 12.

The screw driver 50 defines a plurality external engaging surfaces 58, 58' that engage the drill assembly 30. The external engaging surfaces 58 define upper and lower shoulders 59 that engage the top and bottom surfaces of the screw guide assembly 30, positioning the shaft 51 axially and rotationally with respect to the drill guide assembly 30.

The drill guide assembly 30 is generally L-shaped with a first, screw driver securing end 31 and a second, drill guide end 33. The first end 31 includes a channel 32 that defines a plurality of interior engaging surfaces 34, 34' for removably receiving the screw driver 50.

In the embodiment shown, the screw driver 50 has transverse opposing first and second engaging surfaces 58, 58', respectively. However, it is to be understood, that, in other embodiments, there can be additional external engaging surfaces 58 that then removably mate with a corresponding configuration of additional internal engaging surfaces 34, 34' on the screw guide assembly 30.

The second end 33 of screw guide assembly 30 defines an axially extending threaded opening 35 which is configured to receive a threaded tightening mechanism 37. When advanced toward the channel 32, a distal end 39 (seen in FIG. 1) of the tightening mechanism 37 contacts the first external surface 58 of screw driver 50, securing and aligning the screw guide assembly 30 to the driver 50.

Referring again to FIG. 1, following the cannulated screw 12 placement, a small incision is made to allow for a drill guide wire "B" using the drill guide assembly 30.

The drill guide assembly 30 has a slotted arcuate section 42 that defines an arcuate opening 43 for positioning of a drill guide bushing assembly 44. The drill guide bushing assembly 44 includes a drill guide 46 having a threaded portion 46a that engages a securing portion 46b and a thumbwheel portion 46c. The threaded portion 46a, the securing portion 46c and the thumbwheel portion 46c each define internal openings through which a cannulated drill bit guide 48 can be received.

The drill guide bushing assembly 44 can be slidably positioned along the arcuate opening 43, and be secured in place with the thumbwheel portion 46c. In use, the curves of the arcuate section 42 are centered on the center of the transverse opening 14 in the screw 12, when the screw 12 is fixed to the driver 50 and the driver 50 is fixed to the drill guide assembly 30. In this way a drill guide wire (shown as "B", or a drill bit (shown as "D") passing through the cannulated drill bit guide 48 and the drill guide bushing assembly 44 also passes through the transverse opening 14 in the screw 12. The drill guide bushing assembly 46 can be slidably moved in order to provide support for the drill bit "D" as close to the bone as possible. The procedure is to align the drill guide assembly 30, push through a drill guide wire "B", then drill over that wire with a cannulated drill bit "D". In certain embodiments, two sizes of cannulated drill bit guides 48 are needed, one for the wire and a larger one for the drill.

The cannulated drill bit guide 48 is then always pointing at the center of the transverse opening 14. The surgeon then sets this drill trajectory with two adjustments. First, she can rotate the screw driver 50 and screw 12 as a unit to rotate the trajectory about the screw axis. Second, she can loosen the thumbwheel portion 46c and slide the drill bushing assembly 46 along the arcuate opening 43 to adjust the trajectory about an axis generally perpendicular to the frontal plane. After the through hole is drilled through the patient, the driver 50 and the SAFFR fixation/reconstruction drill guide assembly 30 can be taken away, unless there is some value in using either or both to guide the insertion of the tension band 18.

It is to be understood that FIG. 1 schematically illustrates the tension band 18, the driver 50 and the SAFFR fixation/reconstruction system 10 in order to show their relative positions; but—in reality, during use, by the time the tension band 18 is installed, the driver 50 and the SAFFR fixation/reconstruction system 10 would normally have been removed.

Referring again to FIG. 1, during the fixation/reconstruction procedure the drill guide wire "B" is punched through the fibula, the transverse opening 14 in the screw 12, and the tibia. The drill guide wire "B" serves as a guide for the cannulated drill bit guide 48. The cannulated drill bit "D" is then used to create a transverse-extending passage through the patient's leg (i.e., through the skin, fibula and tibia) for ultimately receiving the tension band 18.

Following the drilling, the tension band 18 is guided through the lateral side of the tibia, through the transverse opening 14 in the cannulated screw 12, through the fibula, and eventually retrieved on the medial side of the tibia.

On the medial side of the tibia, a small incision is made to allow retrieval and access to the tension band 18 and placement of a first fastener 22. The medial end of the tension band 18 is then secured to the fastener 22 through knotting, swaging, or other means. The fastener 22 prevents the tension band 18 from being pulled back through the drilled hole, allowing the tension band 18 to be tensioned in the next step. The drill guide bushing assembly guide 30 is then able to be removed.

A second fastener 24 is then positioned where the tension band 18 emerges from the lateral aspect of the fibula. The tension band 18 is tensioned against the fibula, drawing the fibula and tibia together to correct the syndesmosis tear. When the correction is judged complete, the tension band 18 is fixed to the second fastener 24 with knotting, swaging, or other means, securing the repair.

Figure 7:
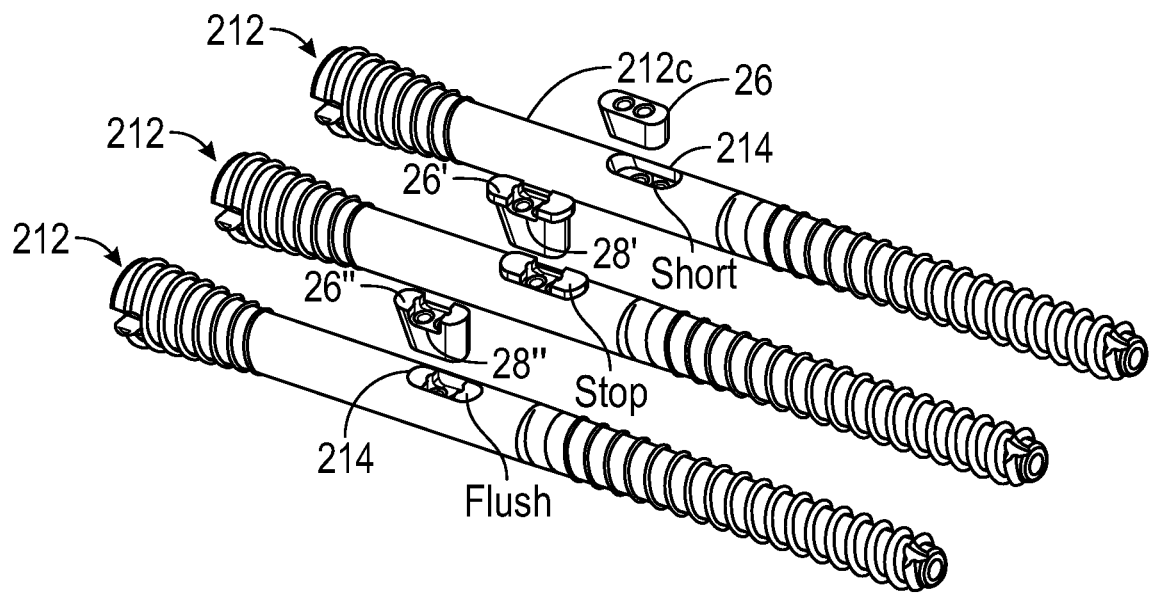
FIG. 7. Schematic exploded perspective views of screw with: a short lateral wedge (top); a stop lateral wedge (middle); and, a flush lateral wedge (bottom).
Figure 8:
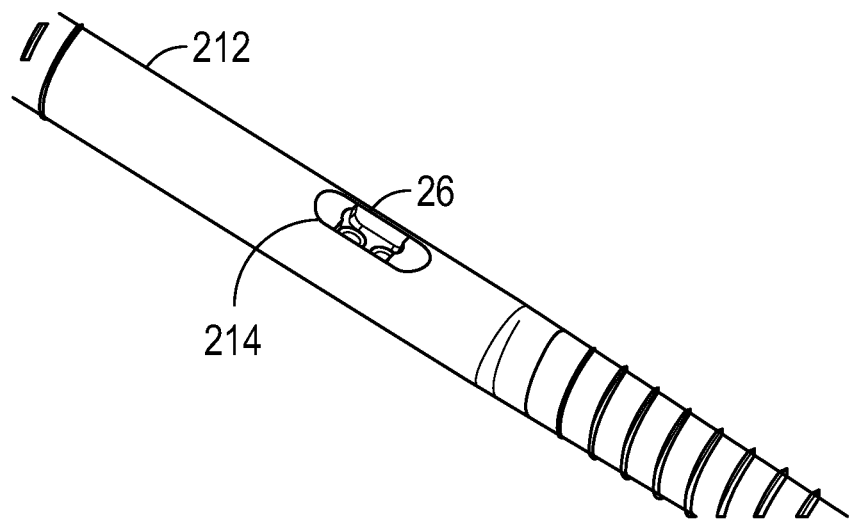
FIG. 8. Schematic perspective partial view of a screw having a flush lateral wedge inserted therein.

If the fibula bone in the area is damaged so as to be unable to support the second fastener 24, the second fastener 24 can be secured directly to the screw 12, and provide the same therapeutic result. Also, in certain embodiments, as shown in FIGS. 7-8, the tension band 18 can be secured in the opening 14 with a wedge 26, 26', or 26" that is configured to engage the transverse opening 14. For example, certain wedges 26', 26" can have a recessed area 28', 28", respectively, to contain knotting of the tension band 18. FIG. 7 shows perspective views of screws with: a short lateral wedge 26 (top); a stop lateral wedge 26' (middle); and, a flush lateral wedge 26" (bottom). FIG. 8 shows a schematic perspective partial view of a screw having a wedge 26 inserted therein.

If necessary, one or more tension bands and/or fasteners can be added above or below the first tension bands and fasteners. In such embodiments, the screw 12 has more than one transverse opening 14.

Referring now to FIGS. 3-8, there are several types of cannulated screws that are well-adapted for use with the fixation/reconstruction device. Each has different features.

Figure 3:
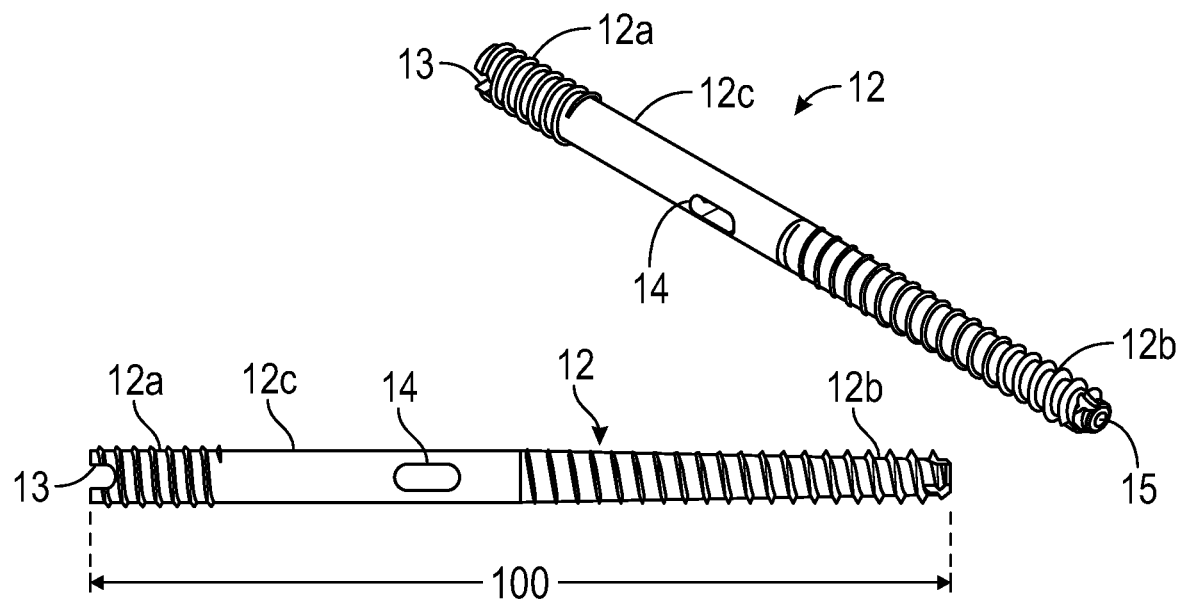
FIG. 3. Schematic perspective (top) and side-elevational (bottom) views of a headless compression screw.

FIG. 3 shows a headless compression cannulated screw 12 which is tapered, and has no head. The cannulated screw 12 has a slot 13 on a first end 12a, at least one transverse opening 14, and an axially extending opening 15 from the first end 12a to a second end 12b of the screw 12.

The screw 12 is threaded in both the first end (head region) 12a and the second end (tip region) 12c, with a non-threaded region 12c between. This screw 12 is useful for distal fibula transverse fractures with fracture lines located within the non-threaded region. The threads in the head region 12a are of greater diameter and smaller pitch than the threads in the tip region 12b. As the threads of the head region 12a enter the bone, they advance more slowly due to this decreased pitch. This causes the bone fragment engaged by the head region 12a to be drawn towards the fragment engaged by the tip region 12b, reducing the fracture.

Figure 4:
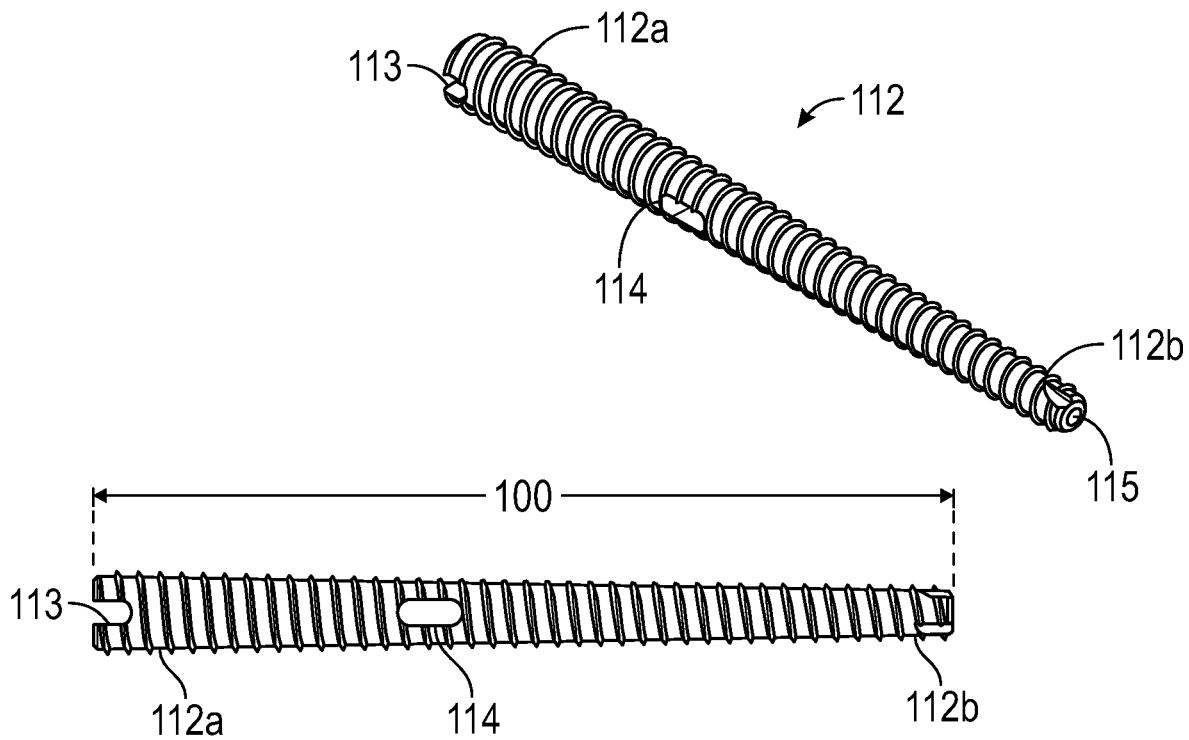
FIG. 4. Schematic perspective (top) and side-elevational (bottom) views of a headless full thread screw.

FIG. 4 shows a headless full thread cannulated screw 112. The cannulated screw 112 has a slot 113 on a first end 112a, at least one transverse opening 114, and an axially extending opening 115 from a first end 112a to a second end 12b of the screw 12. The screw 112 is tapered from the first end (head region) 112a to the second end (tip region) 112b. This screw 112 does not have a compression function. This screw 112 is used for distal tibia commuted fractures, with syndesmosis injury.

Figure 5:
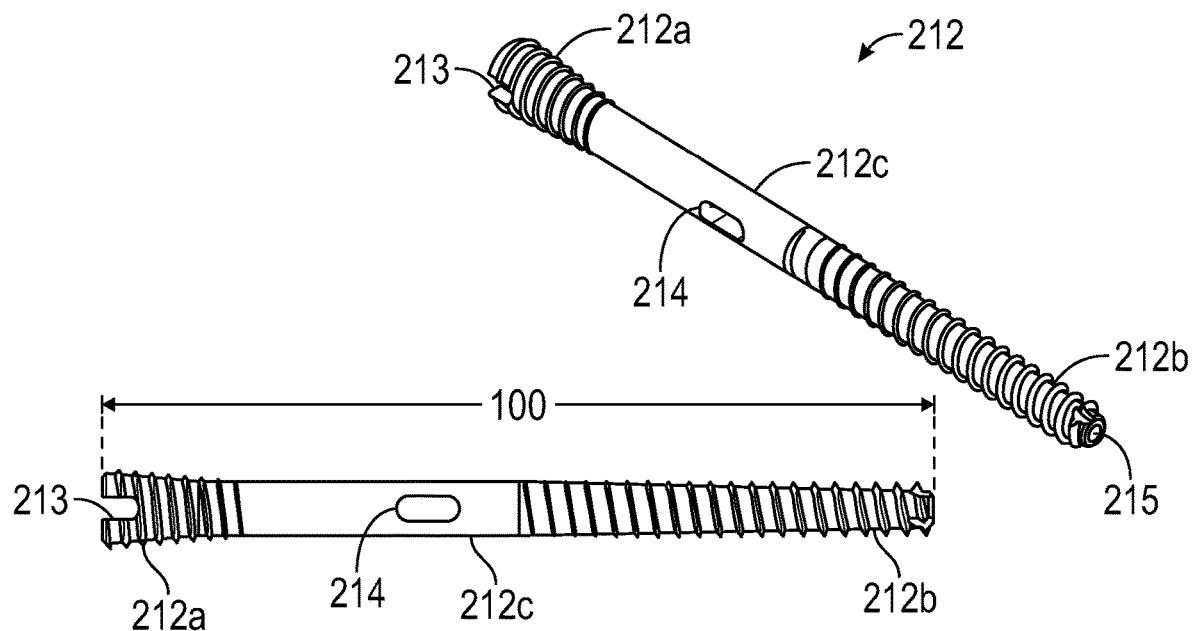
FIG. 5. Schematic perspective (top) and side-elevational (bottom) views of a head compression screw.

FIG. 5 shows a headed compression cannulated screw 212 which has a slot 213 on a first end 212a, at least one transverse opening 214, and an axially extending opening 215 from the first end 212a to a second end 212b of the screw 212.

The headed compression cannulated screw 212 has a significantly larger diameter at the first end (head region) 212a as compared to the second end (tip region) 212b, and is threaded in both the head and tip regions. The middle portion 212c has no threading for improved strength. The tip region 212a of this screw 212 is tapered. The threads in the head region 212a are of greater diameter and smaller pitch than the threads in the tip region 212b. As the threads of the head region 212a enter the bone, they advance more slowly due to this decreased pitch. This causes the bone fragment engaged by the head region 212a to be drawn towards the fragment engaged by the tip region 212b, reducing the fracture. This screw 212 is used for lateral malleolus fracture and distal fibular transverse type syndesmotic ankle fractures. This screw 212 has stronger compression capabilities to improve healing.

Figure 6:
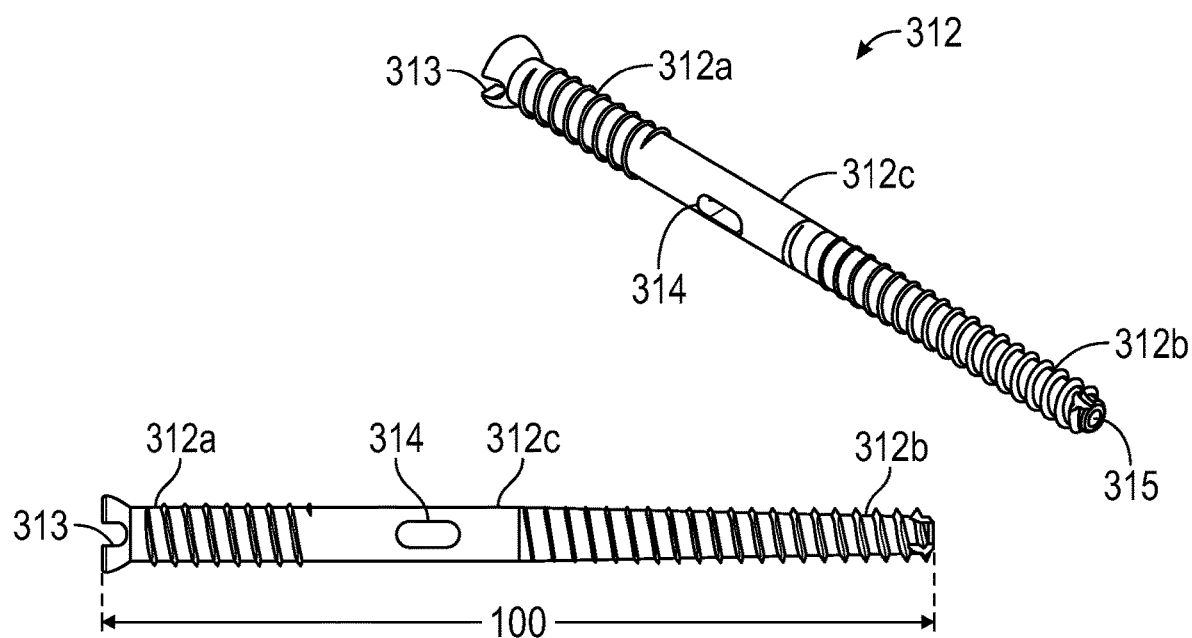
FIG. 6. Schematic perspective (top) and side-elevational (bottom) views of a head non-compression screw.

FIG. 6 shows a headed non-compression cannulated screw 312 which has a slot 313 on a first end 312a, at least one transverse opening 314, and an axially extending opening 315 from the first end 312a to a second end 312b of the screw 312.

The first end (head region) 312a has same threading in distal 313a and proximal portions 313b. This screw 312 does not compress. This screw 312 is used for reconstruction of syndesmosis injury and lateral malleolus fracture.

Kits

In certain embodiments, the fixation/reductions device is provided in the form of a sterilized kit. The kit may include, one or more of the following: the SAFFR fixation/reconstruction driver 50; drill guide assembly 30; one or more types of screws 12; one or more types of tension bands 18; one or more types fasteners, 22, 24; one or more types of wedges 26, 26'; one or more types of screw-guide wires "S"; one or more types of drill guide wires "B"; and, one or more types of drill bits "D".

Uses

The SAFFR fixation/reconstruction device provides a minimally invasive technique, allowing simultaneous reduction and fixation of distal fibular fracture, and reconstruction of the disrupted syndesmotic ligaments in patients with syndesmotic ankle fractures.

Use of this SAFFR fixation/reconstruction device decreases chances of relevant risk factors such as infection, delayed union, and non-union. Further, this minimally invasive fixation/reconstruction device allows for use on patients with significant comorbidities and soft tissue damage safely.

The SAFFR fixation/reconstruction device combines the procedures of reduction and fixation of distal fibular fracture and reconstruction of the disrupted syndesmotic ligaments simultaneously, while employing a minimally invasive approach. SAFFR device also provides improved reduction and reduction maintenance when compared to syndesmosis screws.

With use of the SAFFR fixation/reconstruction device, there is often no need for a second operation for routine implant removal. Also, use of the SAFFR fixation/reconstruction device in fixation/reconstruction procedures allows for earlier physiologic motion of the ankle and syndesmosis following the fixation/reconstruction procedure. Further, use of the SAFFR fixation/reconstruction device supports early weight-bearing and accelerated rehabilitation and recovery.

The SAFFR fixation/reconstruction allows percutaneous insertion, and may be safely used in high-risk patients, such as patients with significant comorbidities and soft tissue damage Implementation of the SAFFR fixation/reconstruction can decrease chances of complications such as infection and delayed union or non-union, due to its minimally invasive approach While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof.

Therefore, it is intended that the invention not be limited to the particular embodiment disclosed herein contemplated for carrying out this invention, but that the invention will include all embodiments falling within the scope of the claims.

What is claimed is:

1. A fixation/reconstruction system comprising:
   a drill guide assembly comprising
      a screw driver securing end having a channel that defines a plurality of interior engaging surfaces for removably receiving a screw driver, a tightening mechanism to secure the screw driver in the channel, a drill guide bushing assembly including a threaded portion that engages a securing portion having a thumbwheel portion, wherein the threaded portion, the securing portion, and the thumbwheel portion each defines an internal opening, wherein the internal openings are aligned, a slotted arcuate section that defines an arcuate opening for positioning of the drill guide bushing assembly, and a cannulated drill bit guide configured to be received by the aligned internal openings of the drill guide bushing assembly;

a cannulated screw having a slot on a head end, at least one transverse opening, and an axially extending opening from the head end to a tip end of the cannulated screw;

a wedge having two parallel channels therethrough and being configured to engage the transverse opening;

a tension band; and one or more fasteners.

2. The fixation/reconstruction system of claim 1, wherein:
the drill guide assembly has the screw driver securing end and a drill guide end, the drill guide end defining a threaded opening configured to receive the tightening mechanism;
the tightening mechanism is threaded and has a distal end, wherein the tightening mechanism is configured to be able to be advanced toward the channel whereby, when the screw driver is within the channel, the distal end contacts the screw driver;
the drill guide end of the drill guide assembly has the slotted arcuate section; and
the drill guide bushing assembly is configured to be slidably positioned along the arcuate opening and to be secured in place with the thumbwheel portion.

3. A method for treating syndesmotic ankle fractures using the fixation/reconstruction system of claim 2, the fixation/reconstruction system including a screw driver, the method comprising:
removably placing a screw-guide wire "S" into an intramedullary space of a distal fibula of an ankle, the guide wire "S" serving as a guide for the cannulated screw;
inserting the cannulated screw into the intramedullary space of the distal fibula;
securing the cannulated screw to prevent rotation within the fibula by removably engaging the slot of the cannulated screw with a tip of the screw driver by engaging a shaft of the screw driver within the channel defined by the plurality of interior engaging surfaces of the drill guide assembly, and securing the shaft by advancing a distal end of the tightening mechanism in a direction toward the shaft;
aligning the drill guide end of the drill guide assembly to a position adjacent the at least one transverse opening in the cannulated screw by positioning the drill guide bushing assembly along the arcuate opening in the slotted arcuate section;
passing a drill guide wire "B" through the cannulated drill bit guide, through the fibula, through the at least one transverse opening in the cannulated screw within the fibula; and through a tibia; the drill guide wire "B" serving as a guide for a cannulated drill to create a passage for the tension band;
forming the passage through the fibula and the tibia with the cannulated drill;
guiding a first end of the tension band through the fibula, through the at least one transverse opening in the cannulated screw, and through the tibia, and retrieving the first end of the tension band on a medial side of the tibia;
placing a first fastener of the one or more fasteners along a central portion of the tension band;
guiding the first end of the tension band back through the tibia, the at least one transverse opening of the cannulated screw, the fibula, and out of a patient's leg; and,
placing a second fastener of the one or more fasteners on the tension band, and securing the first end and a second end of the tension band, thereby allowing tightening and treatment of a syndesmosis.

4. The fixation/reconstruction system of claim 1, further including one or more of: a screw-guide wire "S"; a drill guide wire "B"; and the screw driver.

5. The fixation/reconstruction system of claim 4, including the screw driver, wherein:
the screw driver has a shaft and a tip;
the tip has an axially extending threaded tightening mechanism;
the tip has opposing ears that are configured to engage the slot on the head end, providing a means to transmit torque to drive the cannulated screw and to align the cannulated screw to the drill guide assembly; and
the shaft defines a plurality of external engaging surfaces that have upper and lower shoulders that are configured to engage the drill guide assembly, positioning the shaft axially and rotationally with respect to the drill guide assembly.

6. The fixation/reconstruction system of claim 1, wherein the cannulated screw, the drill guide assembly, the tension band, and the one or more fasteners are packaged as a sterilized kit.

7. The fixation/reconstruction system of claim 1, wherein the cannulated screw, the drill guide assembly, the tension band, the one or more fasteners, a screw-guide wire "S", a drill guide wire "B", and the screw driver are packaged as a sterilized kit.

8. The fixation/reconstruction system of claim 1, wherein the cannulated screw is tapered and threaded on both the head end and the tip end, and has a non-threaded region between the head end and the tip end; and,
wherein threads of the head end are of greater diameter and smaller pitch than threads of the tip end.

9. The fixation/reconstruction system of claim 1, wherein the cannulated screw is a headless full thread cannulated screw and is tapered from the head end to the tip end.

10. The fixation/reconstruction system of claim 1, wherein the cannulated screw is a headed compression cannulated screw having a diameter at the head end that is larger than the diameter of the tip end, and is threaded in both the head and tip ends; and, wherein the threads in the head end are of greater diameter and smaller pitch than the threads in the tip end.

11. The fixation/reconstruction system of claim 1, wherein the cannulated screw is a headed non-compression cannulated screw having the same threading in distal and proximal portions.

12. The fixation/reconstruction screw of claim 1, wherein the cannulated screw comprises a headless full thread cannulated screw wherein the headless full thread cannulated screw is tapered from the head end to the tip end.

13. The fixation/reconstruction screw of claim 1, wherein the cannulated screw comprises a headed non-compression cannulated screw having the same threading in distal and proximal portions.

14. A method for treating syndesmotic ankle fractures using the fixation/reconstruction system of claim 1, the method comprising:
- removably inserting a screw-guide wire "S" into an intramedullary space of a distal fibula of an ankle, the guide wire "S" serving as a guide for the cannulated screw;
- inserting the cannulated screw into the intramedullary space of the distal fibula;
- inserting a drill guide wire "B" through the at least one transverse opening in the cannulated screw;
- drilling through the distal fibula and a tibia to create a passage for the tension band;
- guiding a first end of the tension band through the passage in the fibula, the at least one transverse opening in the cannulated screw, and the passage in the tibia, and retrieving the first end of the tension band on a medial side of the tibia;
- placing a first of the one or more fasteners along a central portion of the tension band;
- guiding the first end of the tension band back through the tibia, the opening of the cannulated screw, and the fibula;
- placing a second fastener of the one or more fasteners on a second end of the tension band; and,
- securing the first and second ends of the tension band, thereby allowing tightening and treatment of a syndesmosis.

15. The fixation/reconstruction system of claim 1, wherein the wedge is configured to secure the tension band in the transverse opening.

16. The fixation/reconstruction system of claim 1, wherein the wedge includes a recessed area configured to contain knotting of the tension band.

17. A fixation/reconstruction system comprising:
- a drill guide assembly comprising
    - a screw driver securing end having a channel that defines a plurality of interior engaging surfaces,
    - a tightening mechanism configured to secure a screw driver in the channel,
    - a drill guide bushing assembly including a threaded portion that engages a securing portion having a thumbwheel portion, wherein the threaded portion, the securing portion, and the thumbwheel portion each defines an internal opening, wherein the internal openings are aligned,
    - a slotted arcuate section that defines an arcuate opening for positioning of the drill guide bushing assembly, and
    - a cannulated drill bit guide configured to be received by the aligned internal openings of the drill guide bushing assembly;
- a cannulated screw having at least one transverse opening;
- a tension band;
- a wedge having two parallel channels therethrough and being configured to secure the tension band in the transverse opening; and
- one or more fasteners.

* * * * *